United States Patent [19]

Adachi et al.

[11] 4,190,728
[45] Feb. 26, 1980

[54] PROCESS FOR THE PRODUCTION OF LOWER ALKYL 2-CHLORO-2-HYDROXYIMINOACETATES

[75] Inventors: Ikuo Adachi, Suita; Teruo Yamamori; Yoshiharu Hiramatsu, both of Nishinomiya, all of Japan

[73] Assignee: Shionogi & Co., Ltd., Osaka, Japan

[21] Appl. No.: 895,476

[22] Filed: Apr. 11, 1978

[30] Foreign Application Priority Data

May 2, 1977 [JP] Japan .................................. 52-50939

[51] Int. Cl.² ........................................... C07C 131/00
[52] U.S. Cl. .................................. 560/168; 548/246; 548/248
[58] Field of Search ........................................ 560/168

[56] References Cited

U.S. PATENT DOCUMENTS

| 3,211,742 | 10/1965 | Lenaers | 560/168 |
| 3,218,331 | 11/1965 | Eloy | 560/168 |
| 3,504,017 | 3/1970 | Breslow | 560/168 |
| 3,584,032 | 6/1971 | Fuchs | 560/168 |
| 3,686,280 | 8/1972 | Rave | 560/168 |
| 3,742,036 | 6/1973 | Perronnet | 560/168 |

*Primary Examiner*—Bernard Helfin
*Assistant Examiner*—Michael Shippen
*Attorney, Agent, or Firm*—Birch, Stewart, Kolasch and Birch

[57] ABSTRACT

Lower alkyl 2-chloro-2-hydroxyiminoacetates are produced by (A) reacting chloral with a lower alkanol and a hydroxylamine salt in the presence of a Lewis acid or a metal oxide which is convertible into said Lewis acid during the course of the reaction to give a lower alkyl 2-hydroxyiminoacetate and then chlorinating the resulting product or (B) reacting chloral oxime with a lower alkanol in the presence of a base to give a lower alkyl 2-hydroxyiminoacetate and finally chlorinating the thus formed product.

9 Claims, No Drawings

PROCESS FOR THE PRODUCTION OF LOWER ALKYL 2-CHLORO-2-HYDROXYIMINOACETATES

The present invention relates to a novel process for the production of lower alkyl 2-chloro-2-hydroxyiminoacetates, and its object is to provide synthetic intermediates for 1,1-dimethyl-3-(5-t-butyl-3-isoxazolyl)urea (U.S. Pat. No. 4,062,861) and the like which are useful as selective herbicides. The following references disclose prior processes for the production of the lower alkyl 2-chloro-2-hydroxyiminoacetates.

(1) Skinner, J. Am. Chem. Soc., 46, 738 (1924)
(2) Hesse et al., Chem. Ber., 88, 130 (1955)
(3) Breslow et al., J. Org. Chem., 36, 3813 (1971)
(4) Nikolaeva, J. Gen. Chem., USSR, 1646 (1973)

However, the synthetic processes disclosed in these references give a low yield and are less satisfactory for industrial purposes. After diligent investigation for much improved synthetic processes, the present inventors have succeeded in establishing the present invention.

This invention relates to a process for the production of lower alkyl 2-chloro-2-hydroxyiminoacetates (I) which comprises (A) reacting chloral (III) with a lower alkanol (V) and a hydroxylamine salt in the presence of a Lewis acid or a metal oxide which is convertible into said Lewis acid during the course of the reaction to give a lower alkyl 2-hydroxyiminoacetate and then chlorinating the resulting product or (B) reacting chloral oxime (IV) with a lower alkanol (V) in the presence of a base to give lower alkyl 2-hydroxyiminoacetate (II) and chlorinating the thus formed product.

The objective compounds of this invention can be obtained as shown in the following scheme:

Route A
$CCl_3CHO$ (III)

First step | ROH (V)
           | $NH_2OH$ salt
           | (Lewis acid)

Route B
$CCl_3CH=NOH$ (IV)

First step | ROH (V)
           | (Base)

ROCOCH=NOH (II)

Second step | $Cl_2$

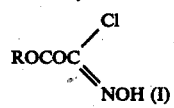
NOH (I)

(wherein R represents a lower alkyl group e.g. methyl, ethyl, propyl, isopropyl, butyl, hexyl).

Route A

The first step can be carried out by reacting chloral (III) with a lower alkanol (V) and a hydroxylamine salt in the presence of a Lewis acid or a metal oxide which is convertible into said Lewis acid during the course of the reaction. The Lewis acid includes calcium chloride, magnesium chloride, aluminum chloride, stannic chloride, zinc chloride, titanium tetrachloride and ferric chloride; and the metal oxide which is convertible into the Lewis acid includes magnesium oxide and zinc oxide. A suitable ratio of the Lewis acid or metal oxide to chloral (III) is about 0.8 to about 1.1 molar equivalent. The lower alkanol (V) includes methanol, ethanol, propanol, isopropanol, butanol, isobutanol and hexanol. And the hydroxylamine salt includes hydroxylamine sulfate, hydroxylamine hydrochloride and the like. The preferable amount of the hydroxylamine salt to chloral (III) is about 1.0 to about 1.2 molar equivalent. This reaction can be effected with heating at around the boiling point of said lower alkanol (V) which also works as a solvent.

The second step comprises chlorination of the above obtained lower alkyl 2-hydroxyiminoacetate (II). This reaction can be carried out at room temperature or with cooling while introducing liquid or gaseous chlorine into the solution of said lower alkyl 2-hydroxyiminoacetate (II) in a suitable solvent (e.g. methylene chloride, chloroform).

Route B

The first step can be carried out by reacting chloral oxime (IV) with a lower alkanol (V) in the presence of a base. The base implies sodium hydrogen carbonate, sodium carbonate, triethylamine and the like. An appropriate amount of the base to chloral oxime (IV) is about 1.5 to about 3.0 molar equivalent. This reaction can be carried out with heating by using a lower alkanol (V) which also works as a solvent.

The second step can be carried out as in the second step of Route A.

Industrial advantages of the present invention over the prior art are shown as follows:

(1) the starting material, chloral, is easily available at a low price;
(2) the operation is simple; and
(3) the yield is excellent.

According to the following reaction scheme, the final product (I) can be converted into, for example, 1,1-dimethyl-3-(5-t-butyl-3-isoxazolyl)urea, a selective herbicide:

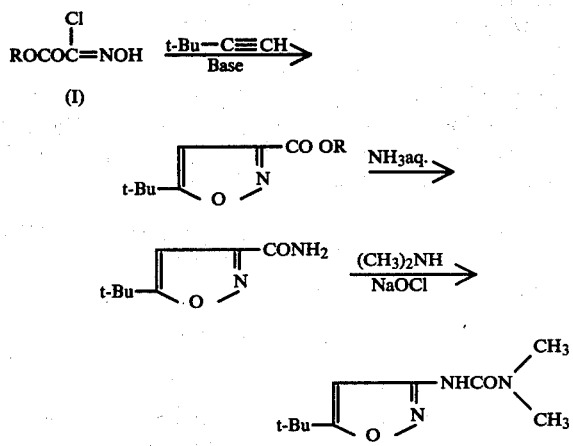

(wherein t-Bu means a tertiary butyl group and R has the significance given above).

The following examples show embodiments of this invention.

EXAMPLE 1

(1) Chloral (7.4 g), hydroxylamine sulfate (4.43 g) and magnesium chloride (3.8 g) are added to ethanol (50 ml) and the resulting mixture is refluxed for 70 hours with heating and stirring. After evaporating the solvent, the residue is mixed with water and the resulting mixture is extracted with ether. The extract is washed with saturated brine, dried over sodium sulfate, and filtered. After evaporating the solvent from the filtrate, the residue is distilled under reduced pressure to give ethyl 2-hydroxyiminoacetate (5.0 g) as a colorless oily product. Yield is 85.3%.

Boiling point: 114°–116° C. (12 mmHg):

IR (CHCl$_3$): 1730 (ester), 3570 (hydroxy) cm$^{-1}$.

(2) Into a solution of the above obtained ethyl 2-hydroxyiminoacetate (1.17 g) in dry methylene chloride (40 ml) is gradually introduced gaseous chlorine (3.6 g) at 0° C. with cooling over a cryogen, and the resulting mixture is stirred below 0° C. for 1 hour and then stirred at room temperature for 1 hour. The product is crystallized from benzene/n-hexane to give ethyl 2-chloro-2hydroxyiminoacetate as colorless needles melting at 75° to 80° C. Yield is 94%.

IR (CHCL$_3$): 1740 (ester), 3550 (hydroxy) cm$^{-1}$

EXAMPLES 2 to 7

(1) Using the following lower alkanols instead of ethanol, the reaction is effected as in above Example 1 (1), whereby the corresponding lower alkyl 2-hydroxyiminoacetates are obtained as shown in Table 1.

Table 1

| Ex. No. | R | b.p. (°C.)/mmHg | IR(CHCl$_3$)cm$^{-1}$ ester | IR(CHCl$_3$)cm$^{-1}$ hydroxy | Yield (%) |
| --- | --- | --- | --- | --- | --- |
| 2 | Me | 100–115/18 | 1746 | 3560 | 73.8 |
| 3 | Pr | 100–126/18 | 1720 | 3550 | 83.8 |
| 4 | i-Pr | 100–112/10 | 1730 | 3575 | 77.7 |
| 5 | Bu | 120–125/10 | 1720 | 3550 | 79.5 |
| 6 | i-Bu | 105–115/10 | 1730 | 3570 | 86.3 |
| 7 | Hex | 103–107/0.3 | 1730 | 3550 | 56.6 |

Note)
The abbreviations in the table have the following significances: Me (methyl group), Pr (propyl group), Bu (butyl group), i- (iso-)

(2) Using the above obtained lower alkyl 2-hydroxyiminoacetates(0.01 mol) instead of ethyl 2-hydroxyiminoacetate and varying the amount of methylene chloride, the chlorination is effected as in Example 1 (2), whereby the corresponding lower alkyl 2-chloro-2-hydroxyiminoacetates are obtained as shown in Table 2.

Table 2

| Ex. No. | R | Amount of methylene chloride (ml) | Yield of crude product (%) | Solvent for re-crystalization | m.p./appearance | IR(CHCl$_3$)cm$^{-1}$ ester | IR(CHCl$_3$)cm$^{-1}$ hydroxy |
| --- | --- | --- | --- | --- | --- | --- | --- |
| 2 | Me | 35 | 95.1 | petroleum ether/isopropyl ether | 52°–55° C./colorless prisms | 1746 | 3530 |
| 3 | Pr | 45 | 82.8 | petroleum ether/isopropyl ether | 40°–45° C./colorless needles | 1742 | 3550 |
| 4 | i-Pr | 45 | 76.3 | — | viscous liquid | 1740 | 3540 |
| 5 | Bu | 50 | 95.5 | petroleum | 53°–57° C. colorless needles | 1754 | 3550 |
| 6 | i-Bu | 50 | 95.0 | — | viscous liquid | 1740 | 3530 |
| 7 | Hex | 60 | 96.6 | petroleum ether | 30°–35° C./colorless needle | 1740 | 3525 |

Note)
The abbreviations in the table have the same significances as above.

EXAMPLE 8

(1) Chloral oxime (5.40 g) and sodium hydrogen carbonate (8.39 g) are added to ethanol (35 ml), and the mixture is heated at 50° C. with stirring for 3 hours and refluxed for 30 minutes. After evaporating the solvent, the residue is mixed with water and the mixture is extracted with methylene chloride. The extract is dried over sodium sulfate and filtered. The solvent is evaporated from the filtrate to give ethyl 2hydroxyiminoacetate (3.71g) as a light yellow oil. Yield is 95.1%.

(2) The above obtained product is chlorinated as in Example 1 (2), whereby ethyl 2-chloro-2-hydroxyiminoacetate is obtained as colorless needles melting at 75° to 80° C.

What is claimed is:

1. A process for the production of a lower alkyl 2-hydroxyiminoacetate which comprises reacting chloral with a lower alkanol and a hydroxylamine salt in the presence of a Lewis acid selected from the group consisting of calcium chloride, magnesium chloride, aluminum chloride, stannic chloride, zinc chloride, titanium tetrachloride and ferric chloride or a metal oxide which is convertible into said Lewis acid during the course of the reaction selected from the group consisting of magnesium oxide and zinc oxide.

2. The process according to claim 1, wherein the lower alkanol is ethanol.

3. The process according to claim 1, wherein the Lewis acid is magnesium chloride.

4. The process according to claim 1, wherein the reaction with chloral is carried out with heating at around the boiling point of the lower alkanol.

5. The process according to claim 1, further including the step of chlorinating said lower alkyl 2-hydroxyiminoacetate to give a lower alkyl 2-chloro-2-hydroxyiminoacetate by introducing liquid or gaseous chlorine into a solution of said lower alkyl 2-hydroxyiminoacetate at room temperature or with cooling.

6. A process for the production of a lower alkyl 2-hydroxyiminoacetate which comprises reacting chloral oxime with a lower alkanol in the presence of a base selected from the group consisting of sodium hydrogen carbonate; sodium carbonate and triethylamine.

7. The process according to claim 6, wherein the reaction of chloral oxime is carried out with heating.

8. The process according to claim 6, further including the step of chlorinating said lower alkyl 2-hydroxyiminoacetate to give a lower alkyl 2-chloro-2-hydroxyiminoacetate by introducing liquid or gaseous chlorine into a solution of said lower alkyl 2-hydroxyiminoacetate at room temperature or with cooling.

9. The process according to claim 6, wherein the lower alkanol is ethanol.

* * * * *